US00PP18015P2

(12) United States Plant Patent

Jonkers et al.

(10) Patent No.: US PP18,015 P2
(45) Date of Patent: Sep. 11, 2007

(54) *IMPATIENS* PLANT NAMED 'SILTE LITPINKA'

(50) Latin Name: *Impatiens walleriana*
Varietal Denomination: Silte Litpinka

(75) Inventors: Johanna B. Jonkers, Andijk (NL); Erik Smit, Enkhuizen (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/410,668

(22) Filed: Apr. 25, 2006

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
(74) *Attorney, Agent, or Firm*—Jondle & Associates, P.C.

(57) ABSTRACT

A new *Impatiens* plant particularly distinguished by large double, pink to pale-pink flowers borne well-above the foliage, medium-green foliage with round leaves, an early flowering response, floriferous throughout the summer, a medium-sized, round, bushy and relatively tight plant habit with good branching ability, is disclosed.

1 Drawing Sheet

Genus and species: *Impatiens walleriana.*
Variety denomination: 'Silte Litpinka'.

BACKGROUND OF THE NEW PLANT

The present invention comprises a new and distinct cultivar of *Impatiens,* botanically known as *Impatiens walleriana,* and hereinafter referred to by the cultivar name 'Silte Litpinka'. The new cultivar originated from a hybridization made in January, 2003 in Andijk, The Netherlands. The female parent was the proprietary bright eye-flowered *Impatiens* plant 'IDY-18-4' (unpatented), while the male parent was the proprietary salmon-flowered *Impatiens* plant 'IDY-29-2' (unpatented). The seeds produced by the hybridization were sown in Andijk, Netherlands, in April, 2003. A single plant selection was chosen for further evaluation and for asexual propagation in July, 2003 in Andijk, The Netherlands.

The new cultivar was created in 2003 in Andijk, The Netherlands and has been asexually reproduced repeatedly by vegetative cuttings and tissue culture in Andijk, The Netherlands and Hillscheid, Germany over a two-year period. 'Silte Litpinka' has not been observed under all possible environmental conditions. The present invention has been found to retain its distinctive characteristics through successive asexual propagations.

Plant Breeder's Rights for this cultivar were applied for in Canada on Oct. 17, 2005 and with the European Union on Nov. 18, 2005.

SUMMARY OF THE INVENTION

The following are the most outstanding and distinguishing characteristics of this new cultivar when grown under normal horticultural practices in Andijk, The Netherlands, and Hillscheid, Germany.

1. Large, double, pale-pink to pink flowers borne well above the foliage;
2. Medium green foliage with round leaves;
3. A medium-sized, round, bushy and relatively tight plant habit;

4. Good branching ability;
5. An early flowering response; and
6. Floriferous throughout the summer.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 10-weeks old in a 12-cm pot grown in a greenhouse in Hillscheid, Germany, in mid-May 2005.

DESCRIPTION OF THE NEW CULTIVAR

The following detailed descriptions set forth the distinctive characteristics of 'Silte Litpinka'. The data which defines these characteristics were collected from asexual reproductions carried out in Hillscheid, Germany. The plant history was taken in mid September on 9- to 10-week old un-pinched plants which had been planted as rooted cuttings in 12-cm pots in mid-July 2005 and grown in a greenhouse at a minimum temperature of 21° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens walleriana* Hook.
*Common name.*—*Impatiens.*

Parentage:
*Female parent.*—'IDY-18-4' a proprietary bright-eye-flowered *Impatiens* plant (unpatented).
*Male parent.*—'IDY-29-2' a proprietary salmon-flowered *Impatiens* plant (unpatented).

Growth:

*Growth and branching habit.*—Medium vigor, round, bushy and relatively tight plant habit; well-branched.

*Height.*—15.5 cm.

*Width.*—16.0 cm.

*Propagation.*—Terminal tips for cuttings.

*Time to produce a finished flowering plant.*—8 weeks for a 12-cm pot.

*Time to initiate and develop roots.*—18 days or less at 22° C.

Branches:

*Average number.*—9.4.

*Length of main branches.*—12 cm to 15 cm.

*Internode length.*—1 cm to 2 cm.

*Diameter of branches* (*at midpoint*).—0.7 cm to 0.9 cm.

*Stem color.*—RHS 145C (pale-green) at the tips, RHS 146D at the middle and RHS 184A (very weakly reddish) near the nodes.

Leaves:

*Arrangement.*—Mainly alternate.

*Size.*—Length: Up to 9 cm. Width: Up to 6.3 cm.

*Shape.*—Broadly elliptical to ovate or rhomboid.

*Apex.*—Acuminate.

*Base.*—Acute.

*Margin.*—Slightly serrate, ciliated.

*Color* (*mature leaves*).—Upper surface: RHS 137B. Lower surface: Weakly marbled with RHS 138B (green) and RHS 185D (dull-purple).

*Color* (*immature leaves*).—Upper surface: RHS 137B or RHS 137D. Lower surface: RHS 138B.

*Texture.*—Smooth, glabrous.

*Venation color.*—Upper surface: Indistinct, possibly RHS 138C. Lower surface: RHS 143C (light-green).

*Petioles.*—Length: 2.5 cm. Diameter: 0.4 cm. Color: Upper surface: RHS 145C. Lower surface: RHS 145C. Texture: Glabrous.

Flower buds:

*Shape.*—Nearly round.

*Size.*—Length: Up to 1.6 cm. Diameter: Up to 1.5 cm.

*Color at tight bud.*—RHS 62A to RHS 62C.

Inflorescence:

*Blooming habit.*—7 to 8 weeks after planting of rooted cuttings.

*Inflorescence type.*—Inflorescences appear solitary in the leaf axils of the upper nodes of the stems.

*Number of flowers per inflorescence.*—3 to 4 flowers or buds in various stages of development.

*Flowering season.*—Continuously flowers, mainly from April to October, depending on light intensity and temperature.

*Lastingness of the individual blooms on the plant.*—5 to 7 days (at 18° C. in a greenhouse in the spring).

*Fragrance.*—None.

*Peduncle.*—Color: RHS 144C (light-green). Size: Length: Up to 7.5 cm. Diameter: Lower end: 0.4 cm. Flower end: 0.2 cm. Texture: Flexible, glabrous.

Flowers:

*Form of corolla.*—Double-type.

*Shape of corolla.*—Rose-like with a tight arrangement of petals.

*Corolla size.*—Diameter: 4.5 cm to 4.8 cm. Depth: 1.8 cm to 2.0 cm.

*Number of petals.*—25 to 30.

Petals:

*Shape.*—Mostly obovate; banner petal is cordate.

*Apex.*—Rounded.

*Base.*—Attenuate or obtuse.

*Margin.*—Entire.

*Size.*—Length: 1.9 cm. to 2.5 cm. Width: 2.1 cm to 2.2 cm. Banner petal width: 2.5 cm.

*Color.*—General: Pink center surrounded by light pink petals. Upper surface: RHS 62A for the petals at the center and RHS 62C for the outer petals. Lower surface: RHS 69C and RHS 62C for the margin petals. Markings: RHS N66B (purple-red) small macule at the base of most petals, RHS N57C (purple-pink) or lighter middle band on the banner petal.

*Texture.*—Smooth, satiny.

Spur:

*Shape.*—Curved, directed downward.

*Color.*—RHS 144A to RHS 144B (light-green).

*Size.*—Length: 2.6 cm to 2.8 cm. Diameter: 0.2 cm at the flower base.

Reproductive organs:

*Stamens.*—Not observed.

*Pistils.*—Style and stigma: Not developed. Ovary: 5-celled. Ovary length: 0.6 cm. Ovary color: RHS 145B (green).

Fruit and seed set: No seed set observed.

Disease and insect resistance: No particular resistance or susceptibility has been observed.

COMPARISON WITH PARENTAL AND COMMERCIAL CULTIVARS

'Silte Litpinka' differs from the female parent 'IDY-18-4' (unpatented) by having pale-pink to pink double flowers, while 'IDY-18-4' has bright-eye, semi-double flowers.

'Silte Litpinka' differs from the male parent 'IDY-29-2' (unpatented), by having pale-pink to pink double flowers, while 'IDY-29-2' has salmon, semi-double flowers.

'Silte Litpinka' differs from the commercial cultivar 'TiLipII' (U.S. Plant Pat. No. 14,808) by having medium-green foliage, while 'TiLipII' has dark-green foliage. Additionally, 'Silte Litpinka' has a tight plant habit, while 'TiLipII' has a vigorous mounded plant habit.

'Silte Litpinka' differs from cultivar 'Didi Appleblossom' (U.S. Plant Pat. No. 15,440) by having deeper pink flowers (particularly, a deeper pink in the middle of the flower) than 'Didi Appleblossom'. Additionally, 'Silte Litpinka' has purple-red macules at the petal bases, while 'Didi Appleblossom' does not have macules.

I claim:

1. A new and distinct cultivar of *Impatiens* plant as shown and described herein.

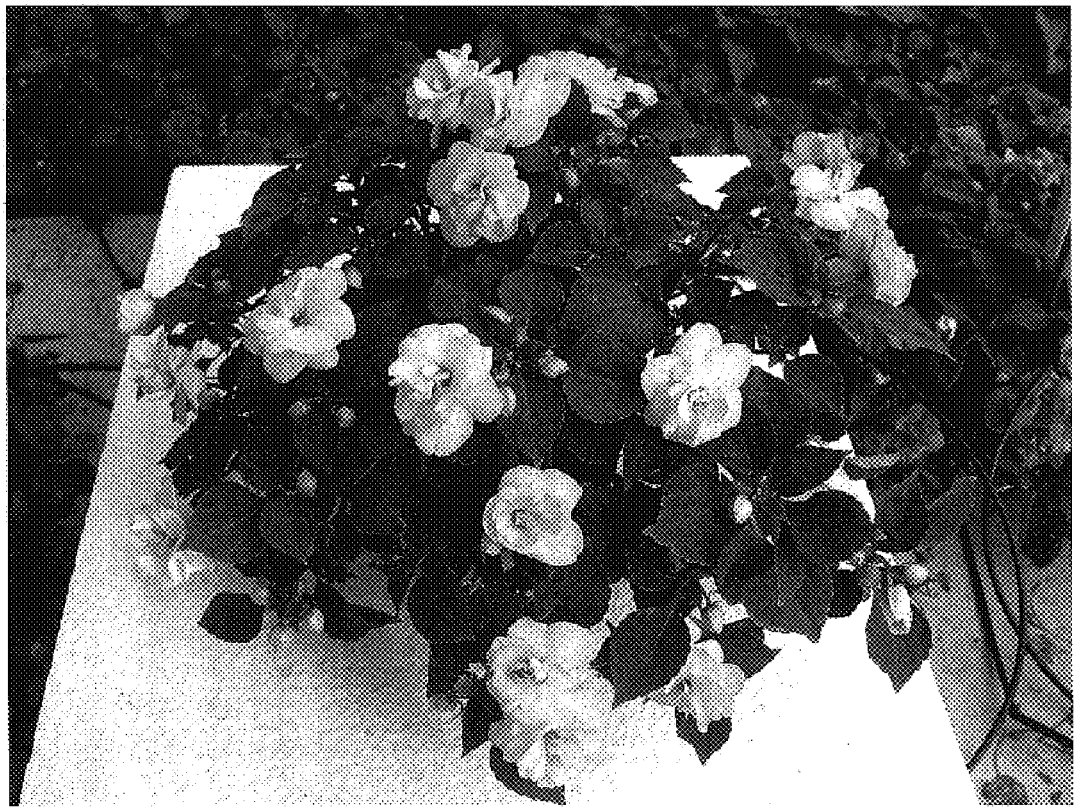

* * * * *